United States Patent [19]

Nakazawa et al.

[11] Patent Number: 4,606,863

[45] Date of Patent: Aug. 19, 1986

[54] PROCESS FOR PREPARING CARBOXYLIC ACID

[75] Inventors: Mikio Nakazawa; Kango Fujitani, both of Uji; Hiroshi Manami, Joyo, all of Japan

[73] Assignee: New Japan Chemical Co., Ltd., Kyoto, Japan

[21] Appl. No.: 616,049

[22] Filed: Jun. 1, 1984

[30] Foreign Application Priority Data

| Jun. 2, 1983 [JP] | Japan | 58-98488 |
| Dec. 13, 1983 [JP] | Japan | 58-235552 |
| Apr. 3, 1984 [JP] | Japan | 59-66970 |

[51] Int. Cl.$^4$ .................. C11C 3/00; C07C 51/23; C07C 51/245
[52] U.S. Cl. .................. 260/413; 562/524; 562/537; 562/538; 562/543; 562/544
[58] Field of Search ............ 260/413, 413 R, 413 HC; 562/537, 538, 524, 543, 544

[56] References Cited

U.S. PATENT DOCUMENTS

| 2,437,648 | 3/1948 | Milas | 260/413 HC |
| 3,076,842 | 2/1963 | Jason et al. | 562/544 |
| 3,173,933 | 3/1965 | Hay | 260/413 |
| 3,362,971 | 1/1968 | Mitchell | 260/413 HC |
| 3,407,221 | 10/1968 | Lutz | 562/544 |
| 3,414,594 | 12/1968 | Dubeck et al. | 260/413 HC |
| 3,557,169 | 1/1971 | Robinson | 562/544 |
| 3,646,130 | 2/1972 | Parshall | 562/543 |
| 3,658,896 | 4/1972 | Washecheck | 562/543 |
| 3,692,810 | 9/1972 | Washecheck | 260/413 HC |
| 3,711,523 | 1/1973 | Pultinas, Jr. et al. | 260/413 |
| 3,816,525 | 6/1974 | Schreyer et al. | 260/413 |
| 3,865,856 | 2/1975 | Dohr et al. | 260/413 |
| 3,910,975 | 10/1975 | Zeidler et al. | 260/413 |
| 3,997,578 | 12/1976 | Sheng | 260/413 |
| 4,098,817 | 7/1978 | Barone | 562/524 |
| 4,532,079 | 7/1985 | Venturello et al. | 562/543 |

FOREIGN PATENT DOCUMENTS

| 32245 | 2/1982 | Japan | 562/544 |
| 322984 | 3/1981 | U.S.S.R. | 562/524 |

Primary Examiner—J. E. Evans
Attorney, Agent, or Firm—Armstrong, Nikaido, Marmelstein & Kubovcik

[57] ABSTRACT

This invention provides a process for preparing carboxylic acid, the process comprising subjecting an oxidation product produced by reacting a peroxide with (a) unsaturated aliphatic monocarboxylic acid having at least one unsaturated bond in the carbon chain and containing 6 to 24 carbon atoms or its ester or (b) cyclic and/or acyclic aliphatic olefin having at least one unsaturated bond in the carbon chain to oxidation by oxygen or oxygen-containing gas in the presence of a catalyst comprising (i) at least one heavy metal compound and (ii) at least one member selected from the group consisting of a bromine compound and a chlorine compound.

24 Claims, No Drawings

PROCESS FOR PREPARING CARBOXYLIC ACID

This invention relates to a process for preparing carboxylic acid and more particularly to a process for preparing aliphatic carboxylic acid by cleaving the double bond of unsaturated aliphatic monocarboxylic acid or its ester or cyclic and/or acyclic aliphatic olefin through oxidation.

It is known to produce dicarboxylic and monocarboxylic acids by cleaving the double bond of unsaturated aliphatic monocarboxylic acid or its ester through oxidation; dicarboxylic acid by cleaving the double bond of cyclic aliphatic olefin through oxidation; and one or two kinds of monocarboxylic acids by cleaving the double bond of acyclic aliphatic olefin through oxidation. The dicarboxylic acid thus produced finds important use as plasticizers or materials for manufacture of polyesters and the monocarboxylic acid as the materials for preparing lubricants. Since the unsaturated carboxylic acid serving as the material for preparing such monocarboxylic and dicarboxylic acids can be easily and inexpensively produced by hydrolysis of animal or vegetable fats and oils, and the aliphatic olefins can be also readily and cheaply manufactured as petrochemical products, it has been desired to develop a commercially advantageous process for preparing monocarboxylic and/or dicarboxylic acid by oxidatively cleaving the double bond of the unsaturated aliphatic monocarboxylic acid or its ester or cyclic and/or acyclic aliphatic olefin.

A process involving the use of ozone, nitric acid, permaganate or like oxidizing agent is known for preparing aliphatic monocarboxylic and/or dicarboxylic acid by cleaving the double bond of unsaturated aliphatic monocarboxylic acid or cyclic and/or acyclic aliphatic olefin through oxidation. However, ozone and permanganate are expensive and commercially disadvantageous to use, and nitric acid, although inexpensive, results in formation of polymerization products in large amount as by-products, consequently giving the carboxylic acid as contemplated in low yields. It is also known to oxidatively cleave the double bond of unsaturated fatty acid by using a hypochlorite or chlorine as the oxidizing agent in the presence of a ruthenium dioxide catalyst (Japanese Unexamined Patent Publication No. 103132/1981). This process, however, has the drawbacks that the chlorine and hypochlorite used as the oxidizing agent and the ruthenium dioxide used as the catalyst are expensive and that the reaction must be conducted in an aqueous basic solution, rendering it difficult to dissolve the starting material therein and to separate the reaction product therefrom.

Attempts have been made to develop a process in which the material is oxidized by air in place of the expensive oxidizing agent. However, the proposed processes in which unsaturated carboxylic acid is directly oxidized (U.S. Pat. No. 2,820,046 and Japanese Examined Patent Publication No. 12767/1965) are unfit for practical purpose because the processes involve a markedly retarded reaction and can not control cleavage site with selectivity.

Improved processes have been proposed which comprise oxidizing unsaturated carboxylic acid or aliphatic olefin by hydrogen peroxide to introduce vicinal diol group onto the double bond of the acid or olefin and then oxidizing the resulting oxidation product by air in the presence of a cobalt salt catalyst (Japanese Unexamined Patent Publication Nos. 1970/1972, 3815/1972, 6014/1972, 9018/1972, 135908/1974 and 135909/1974). These processes, however, have the following drawbacks.

(1) The intermediate material having the vicinal diol group can not be selectively produced with commercial advantage. Generally it is known to introduce vicinal diol group onto the unsaturated bond by causing hydrogen peroxide and water to act on the unsaturated bond in the presence of an acid catalyst to produce vicinal diol group; or by forming an epoxide and then hydrolyzing the epoxide. In the former method, an epoxide is formed as an intermediate in the reaction system and this intermediate epoxide competitively reacts not only with water but also with the co-existing carboxylic acid or alcohol, thus inevitably giving esters, ethers and like oxidation by-products in addition to the desired vicinal diol. The latter method involves many reaction steps and special treatments including the treatment of heating the epoxide together with water and a large amount of fatty acid salt at high temperatures (Japanese Examined Patent Publication No. 57459/1982). Since the vicinal diol of the intermediate can not be selectively produced with commercial advantage as stated above, the desired carboxylic acid is not produced in satisfactory yields.

(2) The foregoing reaction for cleavage of vicinal diol suffer various defects of taking a prolonged induction period, consuming expensive peracetic acid, ketone, aldehyde or other materials, requiring purification of the starting materials and solvent to a considerable extent to achieve continuous reaction, involving the regulation of feed of the starting material and solvent to prevent cease of oxidation, and so on.

It is an object of the present invention to provide a process for preparing the carboxylic acid as contemplated in high yields.

It is another object of the invention to provide a commercially advantageous process for preparing the carboxylic acid.

These objects and other features of the invention will become more apparent from the following description.

This invention provides a process for preparing aliphatic carboxylic acid, the process comprising subjecting an oxidation product produced by reacting peroxide with (a) unsaturated aliphatic monocarboxylic acid having at least one unsaturated bond in the carbon chain and containing 6 to 24 carbon atoms or its ester or (b) cyclic and/or acyclic aliphatic olefin having at least one unsaturated bond in the carbon chain to oxidation by oxygen or oxygen-containing gas in the presence of a catalyst comprising (i) at least one heavy metal compound and (ii) at least one member selected from the group consisting of a bromine compound and a chlorine compound.

With the process of the present invention, even when any of oxygen-containing substituents such as epoxy group; vicinal diol group; hydroxyl group and ester group; hydroxyl group and ether group; ester group and ester group; ether group and ether group; or ester group and ether group; etc. is introduced onto the carbon-carbon double bond of the unsaturated carboxylic acid or aliphatic olefin, the carbon-carbon double bond thereof can be selectively cleft by subjecting the oxidation products produced with use of peroxide to oxidation by molecular oxygen in the presence of the specific catalyst, thereby giving in high yields carboxylic acid corresponding to the unsaturated carboxylic acid or aliphatic olefin whose double bond has been cleft.

The above-mentioned conventional processes (Japanese Unexamined Patent Publication Nos. 1970/1972, 3815/1972, 6014/1972, 9018/1972, 135908/1974 and 135909/1974) are unable to cleave the double bond of the material having groups other than vicinal diol group by oxidation, and thus inevitably necessitate the selective introduction of only the diol group onto the double bond. In contrast, the process of the present invention can selectively cleave the carbon-carbon double bond by oxidation even when the carbon atoms of the double bond have not only vicinal diol but also any of the epoxy group; hydroxyl and ether groups; hydroxy and ester groups; or ester and ether groups; two ester groups or two ether groups and like oxygen-containing substituents as introduced thereonto.

Therefore, the oxidation product to be further oxidized by molecular oxygen according to the invention can be very easily produced by causing a peroxide to act on the unsaturated carboxylic acid or the ester thereof in accordance with the conventional methods. Furthermore, the desired dicarboxylic acid and monocarboxylic acid can be produced in high yields relative to the unsaturated carboxylic acid or the ester thereof. Also the present process can produce the desired dicarboxylic acid in high yields from the cyclic olefin or the desired one or two kinds of monocarboxylic acids in high yields from the acyclic olefin.

The oxidative cleavage of the present invention only employs as a catalyst only a heavy metal (including its various forms, such as its oxide, hydroxide, salt or complex) and a small amount of a bromine compound and/or chlorine compound. It is not necessary to use expensive peracetic acid, ketone, aldehyde, etc. Furthermore, when the present process is conducted as the continuous method, there is no need to purify the starting material or solvent or to regulate the feed so that the reaction will not cease.

Unsaturated carboxylic acids useful in the present invention are aliphatic monocarboxylic acids having at least one carbon-carbon double bond and containing 6 to 24 carbon atoms, such as oleic acid, linoleic acid, linolenic acid, eleostearic acid, parinaric acid, elaidic acid, ricinoleic acid, caproleic acid, myristoleic acid, palmitoleic acid, petroselinic acid, erucic acid, brassidic acid, arachidonic acid, and a mixture thereof, fatty acid mixtures produced by hydrolyzing vegetable oils such as rape seed oil, soybean oil, safflower oil, sesame oil, rice bran oil, corn oil, olive oil, peanut oil, linseed oil, tung oil, etc. or animal oils such as lard, beef tallow, fish tallow, broiler oil, whale oil, etc.; tall oil fatty acid; esters of these fatty acids, particularly methyl ester, ethyl ester, propyl ester or like $C_1$-$C_5$ alkyl ester, glycerides; etc.

Cyclic and/or acyclic aliphatic olefins which can be used as the other starting material for preparing the oxidation products of the present process are those having at least one carbon-carbon double bond and containing 5 to 18 carbon atoms. Examples of suitable olefins are cyclic olefins having 5 to 18 carbon atoms such as cyclopentene, cyclohexene, cyclooctene, dicyclopentadiene, etc. and acyclic olefins having 6 to 18 carbon atoms such as 1-hexene, 3-hexene, 1-heptene, 1-octene, 2-octene, 4-octene, 1-nonene, 1-decene, 5-decene, 6-decene, 1-dodecene, 1-tetradecene, 7-tetradecene, 1-hexadecene, 8-hexadecene, 1-octadecene, 9-octadecene, etc. Dicylopentadiene gives a dicarboxylic acid when only one of the double bonds is oxidatively cleft, or a tetracarboxylic acid when two of the double bonds are oxidatively cleft.

According to the present invention, the foregoing starting material is reacted with peroxide to produce the oxidation product. The oxidation product is formed by introducing oxygen-containing group or groups such as vicinal diol group, epoxy group, hydroxy and ether groups, hydroxy and ester groups, ester and ether groups, two ester groups, two ether groups, etc. onto the two carbon atoms of the carbon-carbon double bond of the starting material. For example, when oleic acid is treated with hydrogen peroxide in the presence of an acid in acetic acid solvent, oxidation products which are mainly formed are as follows:

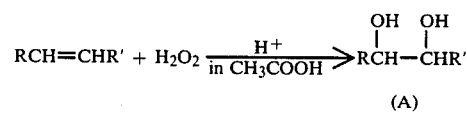

(A)

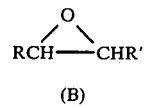

(B)

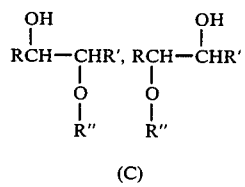

(C)

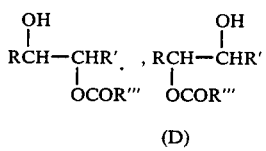

(D)

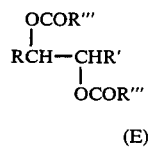

(E)

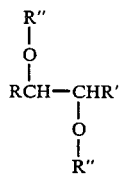

(F)

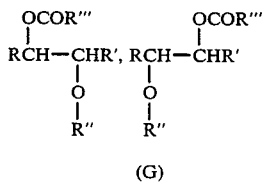

(G)

In the foregoing formula, R is —(CH$_2$)$_7$CH$_3$, R' is —(CH$_2$)$_7$COOH, R" is

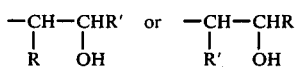

wherein R and R' are as defined above, and R''' is —CH₃,

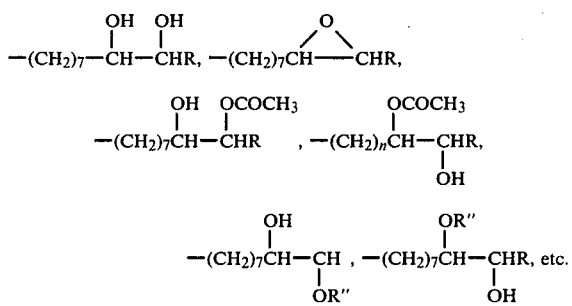

The formula (A) represent an oxidation product having a vicinal diol group, the formula (B) an oxidation product having an epoxy group, the formula (C) oxidation products having hydroxyl and ether groups, the formula (D) oxidation products having hydroxyl and ester groups, the formula (E) oxidation product having ester and ester groups, the formula (F) oxidation product having ether and ether groups, and formula (G) oxidation product having ester and ether groups.

The oxygen-containing substituents can be introduced onto the two carbons of the double bond of the unsaturated aliphatic carboxylic acid or its ester or of the aliphatic olefin by any of methods conventionally used in the art, such as those described by Daniel Swern in "Organic Peroxides", vol. II, P355 (1971), Wiley, or by Juichi Imamura in Journal of the Japan Petroleum Institute, 16, 1058 (1973) or by Juichi Imamura in Journal of the Japan Petrolum Institute, 17, 68 (1974). For example, the introduction of the oxygen-containing substituents can be conducted by reacting the starting maerial with hydrogen peroxide in the presence of formic acid; or by reacting the starting material with hydrogen peroxide in the presence of an acid catalyst in a carboxylic acid; or by reacting the starting material with hydrogen peroxide in the presence of tungstic acid, molybdic acid, vanadic acid or like catalyst; or by effecting reaction after adding water and an organic solvent to the foregoing reaction systems; or by using pertungstic acid, permolybdic acid, permanganic acid or like inorganic peroxide; or by reacting the starting material with cumene hydroperoxide, t-butyl hydroperoxide or like organic hydroperoxide in the presence of molybden, vanadium or tungsten salt catalyst; or by using performic acid, peracetic acid, perbenzoic acid, m-chloroperbenzoic acid or like organic peracid; or by permitting the starting material to coexist with acetaldehyde, benzaldehyde or like aldehyde in the presence of a trace amount of cobalt while feeding molecular oxygen to form organic peracid which is reacted with the starting material, etc. However, the foregoing methods are only exemplary, and any method can be used as far as the method is capable of introducing the oxygen-containing substituent onto the double bond of the unsaturated fatty acid or the ester thereof or the aliphatic olefin.

The reaction mixture obtained by the above method using the peroxide is subjected to a conventional water separation treatment or distilled by the usual method after neutralizing the mineral acid to remove the solvent, followed by separation of water. The resulting oxidation product can be used for the further oxidation reaction according to the invention. If required, the oxidation product is washed with water or topped to remove the remaining hydrogen peroxide or mineral acid.

According to the present invention, the oxidation product thus produced is oxidized by oxygen or an oxygen-containing gas in the presence of the specific catalyst comprising at least one heavy metal compound and at least one member selected from the group consisting of a bromine compound and a chlorine compound. The heavy metal compound, bromine compound and/or chlorine compound can be added to the reaction system at the same time or separately one by one.

Suitable heavy metal compounds can be any of those containing heavy metal having atomic numbers of 23 to 32, 39 to 51 and 57 to 84, among which cobalt, manganese, cerium and nickel are preferable. These heavy metal compounds can be used in any form of metal, salt, complex, oxide and hydroxide. Examples of heavy metal salts are heavy metal salts of an carboxylic acid or an inorganic acid. Examples of the carboxylic acids are formic acid, acetic acid, propionic acid, 2-ethylhexanoic acid, pelargonic acid, stearic acid, oleic acid, adipic acid, azelaic acid and like aliphatic carboxylic acids having 1 to 20 carbon atoms; naphthenic acid; benzoic acid and phthalic acid which may optionally be substituted with halogen atom or methyl group on the phenyl ring; etc. Examples of the inorganic acids are hydrogen chloride, hydrogen bromide, hydrogen iodide, hydrogen fluoride, carbonic acid, sulfuric acid, phosphoric acid, chromic acid, nitric acid, etc. Examples of heavy metal oxides are oxides of cobalt, manganese, nickel or cerium, such as CoO, Co₂O₃, Co₃O₄, MnO, Mn₂O₃, MnO₂, Mn₃O₄, NiO, Ni₂O₃, NiO₂, Ce₂O₃, CeO₂, etc. Examples of heavy metal hydroxides are hydroxides of cobalt, manganese, nickel or cerium, such as Co(OH)₂, Co(OH)₃, Mn(OH)₂, Ni(OH)₄, Ce(OH)₃, Ce(OH)₄, etc. Useful heavy metal complexes include those having as a ligand acetylacetone, ammonia, pyridine, aniline, etc. These heavy metal compounds can be used singly or at least two of them are usable in admixture. Preferred class of heavy metal compounds are metal cobalt, metal manganese, metal cerium, metal nickel; acetate, naphthalene, 2-ethyl-hexanoate, stearate, chloride, bromide or carbonate of cobalt, manganese, cerium or nickel; acetylacetonate complex of cobalt, manganese, cerium or nickel; oxides of cobalt, manganese, cerium or nickel; hydroxides of cobalt, manganese, cerium or nickel.

Suitable bromine compounds are those having at least one bromine atom in the molecule. Useful chlorine compounds are those having at least one chlorine atom in the molecule. These two types of compounds can be used in any form of bromine molecule, chlorine molecule, their acid and salt, and brominated or chlorinated organic compound. Examples of useful acids are hydrogen bromide, hydrogen chloride, etc. Examples of useful salts are bromide, hypobromite, bromate, chloride, chlorate, hypochlorite or perchlorate of ammonia, alkali metal, alkaline earth metal or the heavy metal exemplified above such as cobalt, manganese, cerium, nickel, etc. Suitable brominated organic compounds is lower hydrocarbon bromide and suitable chlorinated organic compound is lower hydrocarbon chloride. Preferred examples of the bromine compounds are hydrogen bromide, ammonium bromide, sodium bromide, cobalt bromide, manganese bromide, cerium bromide, nickel bromide, tetrabromoethane, tribromoethane, etc. Preferred examples of the chlorine compounds are hydrogen chloride, ammonium chloride, sodium chloride, cobalt chloride, manganese chloride, cerium chloride, nickel chloride, tetrachloroethane, trichloroethane, etc. The bromides, hypobromites, bromates, chlorides, chlorates, hypochlorites or perchlorates of heavy metals exemplified above are able to act as the heavy metal compound and at the same time as the bromine compound or chlorine compound when used in the oxidative reaction of the present invention. These bromine compounds and chlorine compounds can be used singly or are usable in admixture.

Preferred catalysts usable in the present invention are given below in detail.

(1) Preferred examples of useful catalysts comprising the heavy metal compound and the bromine compound are powdery metal cobalt and ammonium bromide; cobalt bromide; cobalt acetate and ammonium bromide; cobalt acetate and sodium bromide; cobalt acetate and potassium bromide; cobalt acetate and hydrogen bromide; cobalt acetate and tetrabromoethane; manganese bromide; manganese acetate and hydrogen bromide; manganese acetate and ammonium bromide; manganese acetate and sodium bromide; manganese acetate and tetrabromoethane; etc. Combinations of at least two kinds of heavy metal compounds and bromine compound are advantageous to use because they reduce the induction period and increase the reaction rate. In this case, it is preferable to use at least two heavy metal compounds each of which contain different kind of heavy metal, and which are preferably selected from the preferred class of heavy metal compounds exemplified above in combination with the bromine compound such as one selected from the group consisting of hydrogen bromide, ammonium bromide, sodium bromide, cobalt bromide, manganese bromide, cerium bromide, nickel bromide, tetrabromoethane and tribromoethane. Examples of such catalysts are cobalt bromide and manganese bromide; cobalt bromide and manganese acetate; cobalt acetate and manganese bromide; manganese acetate, cobalt acetate and ammonium bromide; cobalt acetate, manganese acetate and hydrogen bromide; cobalt bromide and cerium acetate; cobalt acetate and cerium bromide; manganese bromide and cerium acetate; cobalt bromide, nickel acetate and ammonium bromide; cobalt acetate, manganese acetate, cerium acetate and ammonium bromide; cobalt naphthenate, manganese naphthenate and tetrabromoethane; cobalt acetyl acetonate, manganese acetylacetonate and hydrogen bromide; cobalt acetate, manganese acetate and sodium bromide; cobalt acetate, manganese acetate, cerium acetate and sodium bromide; cobalt naphthenate, manganese acetate and potassium bromide; etc.

(2) Preferred examples of useful catalysts comprising the heavy metal compound and the chlorine compound are those corresponding to the catalysts exemplified above in (1) above in which the bromine atoms of the heavy metal compound and bromine compound are replaced with chlorine atoms. In this case, it is also preferable to use at least two heavy metal compounds each of which contain different kind of heavy metal and which are preferably selected from the preferred class of heavy metal compounds exemplified above in combination with the chlorine compound such as one selected from the group consisting of hydrogen chloride, ammonium chloride, sodium chloride, cobalt chloride, manganese chloride, cerium chloride, nickel chloride, tetrachloroethane and trichloroethane.

(3) Preferred examples of useful catalyst comprising heavy metal compound, bromine compound and chlorine compound are powdery metal cobalt, ammonium bromide and ammonium chloride; cobalt bromide and cobalt chloride; cobalt acetate, ammonium bromide and ammonium chloride; cobalt acetate, sodium bromide and ammonium chloride; cobalt acetate, potassium bromide and potassium chloride; cobalt acetate, tetrabromoethane and tetrachloroethane; manganese bromide and manganese chloride; manganese acetate, ammonium bromide and ammonium chloride; manganese acetate, hydrogen bromide and hydrogen chloride; manganese acetate, tetrabromoethane and tetrachloroethane; etc. to which the catalysts usable in the present invention are not limited. The use of at least two types of heavy metal compounds is beneficial since their use reduces an induction period and results in increase of reaction rate. In this case, it is preferred to use at least two heavy metal compounds each of which contain different kind of heavy metal and which are preferably selected from the preferred class of heavy metal compounds exemplified above in combination with the bromine compound and chlorine compound. Examples of the bromine compounds are preferably selected from hydrogen bromide, ammonium bromide, sodium bromide, cobalt bromide, manganese bromide, cerium bromide, nickel bromide, tetrabromoethane and tribromoethane. Examples of the chlorine compounds are preferably selected from hydrogen chloride, ammonium chloride, sodium chloride, cobalt chloride, manganese chloride, cerium chloride, nickel chloride, tetrachloroethane and trichloroethane.

It is suitable to use the heavy metal compound in an amount of 0.05 to 10 g calculated as metal per liter of the reaction mixture. If the amount of the heavy metal compounds is less than 0.05 g/liter, an insufficient reaction rate results. If the amount is more than 10 g/liter, the reaction involves an increased cost of the catalyst and forms by-products in an increased quantity. The amount of the bromide compound and/or chlorine compound to be used is 0.1 to 100 equivalents calculated as the bromine atom and/or chlorine atom based on the heavy metal atom. Below 0.1 equivalent, an insufficient reaction rate results. Above 100 equivalents, the reaction forms a product contaminated with bromine and/or chlorine, and incurs an increased cost of the catalyst.

The reaction may be conducted preferably by replenishing bromine compound and/or chlorine compound to prevent the reduction of reaction rate which otherwise would occur when the bromine compound and/or chlorine compound is partially removed from the reaction system by being entrained on exhaust gas during the reaction. In this case, the amount of bromine compound and/or chlorine compound to be newly supplied is 1 wt.%/hr based on the oxidation product when calculated as the bromine and/or chlorine atom.

A solvent is not always required in the reaction of the present invention, but may be used when employing an oxidation product having a high melting point or when it is necessary to eliminate reaction heat. Suitable solvents are polar organic compounds which are inert to or relatively stable to the oxidation under the reaction conditions in the present invention. Examples of such solvents are saturated monocarboxylic acid having about 2 to about 10 carbon atoms among which acetic acid is most preferred.

Suitable oxygen or oxygen-containing gases which are used as the oxidizing agent in the present invention can be any of oxygen-containing gases, including pure oxygen and industrial exhaust gas, among which air is most suited from commercial viewpoint.

The reaction of the present invention is conducted under a total pressure of 0 to 100 kg/cm$^2$G, preferably 2 to 40 kg/cm$^2$G and under an oxygen partial pressure ranging preferably from 0.1 to 10 kg/cm$^2$. To assure safety, it is preferred to effect the reaction such that the exhaust gas discharged from the reactor has an oxygen concentration of 8% by volume or less.

The reaction of the present invention is carried out at a temperature of 60° to 200° C., preferably 80° to 140° C. The reaction at lower than 60° C. proceeds at a lower rate, and at higher than 200° C. results in marked decomposition of the solvent and the reaction product to form carbon dioxide.

The concentration of water in the reaction mixture is preferably maintained at 15 wt.% or less in the present invention. The reaction of the present invention can be conducted either while discharging from the reactor the water produced by the reaction or without resort to removal of the water. When the solvent is repeatedly used, water is accumulated. The reaction, however, can be continued without removal of water until the water concentration reaches 15 wt.%.

The process of the present invention is usually practiced as follows. The material (oxidation product produced by reacting peroxide with unsaturated carboxylic acid or its ester or aliphatic olefin), a catalyst and, when required, a solvent are placed in a reactor equipped with an inlet for gas, an outlet for gas and a stirrer. The air in the reactor is replaced with oxygen or oxygen-containing gas or the reactor is pressurized by oxygen or oxygen-containing gas. Then the mixture in the reactor is heated to the above-specified temperature. It is not always necessary to stir the mixture or to force gas into the mixture while elevating the temperature of the mixture. The absorption of oxygen is initiated usually at a temperature of 60° to 100° C. although its initiation time is variable depending on the type of the catalyst as used, its concentration and the composition of the material. Upon initiation of oxygen absorption, oxygen or oxygen-containing gas is introduced in the reaction system to continue reaction while maintaining the partial pressure of oxygen at a level in the specified range. Exhaust gas is cooled by a condenser and the condensate is returned to the reactor or is partially or wholly run off out of the reactor to remove the water formed.

The reaction can proceed by feeding bromine compound and/or chlorine compound to the reactor only at the commencement of the reaction without subsequent addition of such compound. However, when it is desired to conduct the reaction at an increased rate, the compounds are preferably added subsequently in small amounts as the reaction proceeds. When such compound is replenished, liquids such as tetrabromoethane, tetrachloroethane or the like are supplied as they are, and solids such as ammonium bromide, ammonium chloride or the like are fed as dissolved in water or a solvent. The replenishment of these compounds is carried out continuously or intermittently by a pump. After completing the reaction continuing over a specified period of time, the reaction mixture is cooled and then withdrawn. The reaction mixture is subjected to fractionation at reduced pressure to separate the solvent and monocarboxylic acids. Thereafter, the residue is extracted with hot water or petroleum ether and the extract is recrystallized from water to give dibasic acids. When the oxidation product prepared from the ester of carboxylic acid is used, the resulting reaction mixture obtained after the oxidation by oxygen or oxygen-containing gas is then subjected to hydrolysis to hydrolyze the remaining ester. Thereafter the desired dicarboxylic acids are collected.

In the present invention, it is possible to use a gas-bubble column-type reactor as well as the reactor equipped with a stirrer as stated above. According to the present invention, the reaction can be conducted not only batchwise but also continuously. To achieve continuous reaction in the present invention, the oxidation product, catalyst and, if required, solvent are continuously fed to the reactor and oxygen or oxygen-containing gas is forced into the reaction mixture during the reaction, followed by continuous withdrawal of the reaction product upon completion of the reaction. The present invention eliminates the need to purify the starting material and solvent and requires no regulation in the rate of supply of the starting material and solvent.

The present invention will be described in greater detail with reference to Examples and Comparison Examples.

EXAMPLE 1

To 100 g of commercial oleic acid (iodine value 91) were added 67 g of acetic acid, 34 g of water and 0.3 g of concentrated sulfuric acid, and the resulting mixture was stirred. A 23 g quantity of 60% aqueous solution of hydrogen peroxide was added dropwise to the mixture over a period of 1 hour. The mixture was further stirred with heating at 80° C. for 3 hours. Then sodium hydroxide was added to the mixture to neutralize sulfuric acid, and the acetic acid and water were distilled off under reduced pressure. The residue was washed with water and dried, giving 114 g of an oily substance. Analysis of the oily substance showed that it had an iodine value of 1.5, a vicinal hydroxyl value of 169 and a vicinal hydroxyl value after saponification of 236.

Half of the oily substance (57 g), 50 g of acetic acid, 0.33 g of cobalt bromide (CoBr$_2$.6H$_2$O) and 0.25 g of manganese acetate (Mn(OAc)$_2$.4H$_2$O) were placed into a 500 ml titanium autoclave equipped with a stirrer, and air was introduced into the autoclave to maintain the oxygen partial pressure at 1.5 kg/cm$^2$ (total reaction pressure 25 kg/cm$^2$G) and the mixture was stirred with heating for air oxidation reaction. At a temperature of about 80° C., absorption of oxygen started. The reaction system was maintained at a temperature of 100° C. At each time of one hour and two hours after the start of the reaction, 0.4 ml of a 20% aqueous solution of ammonium bromide was added to the reaction system through a paste pump. When the reaction was conducted for a total of 3 hours, oxygen absorption almost ceased, and then the reaction system was cooled. Acetic acid was distilled off from the reaction mixture. A portion of the reaction mixture was withdrawn, methyl-esterified and analyzed by gas chromatography. According to the analysis, yields of dicarboxylic acids were 70% for azelaic acid, 14% for dibasic acids containing up to 8 carbon atoms and 15% for dibasic acids containing not less than 10 carbon atoms (total 99%), and yields of monocarboxylic acids were 71% for pelargonic acid, 23% for monocarboxylic acids containing 5 to 8 carbon atoms and 5% for monocarboxylic acids containing not less than 10 carbon atoms (total 99%), each relative to the unsaturated fatty acids contained in the starting commercial oleic acid.

The reaction mixture was extracted with petroleum ether, and the remaining crystals were suction filtered and recrystallized from water, giving white crystals of azelaic acid having a purity of 82% and melting at 97° to 101° C. Yield 80% relative to the unsaturated fatty acids contained in the oleic acid.

EXAMPLE 2

To commercial oleic acid (100 g) was added 6 g of 88% aqueous solution of formic acid, and 25 g of 60% aqueous solution of hydrogen peroxide was added dropwise over a period of 1 hour while stirring the mixture at a temperature of 50° to 60° C. The mixture was reacted at the same temperature for 8 hours, cooled, and separated, giving 112 g of an oily substance, which was found by analysis to have an iodine value of 1.5 and oxirane oxygen content of 1.7 g% (epoxide yield 29.8%).

Half of the oily substance, 100 g of acetic acid, 0.19 g of cobalt acetate $(Co(OAc)_2 \cdot 4H_2O)$, 0.18 g of manganese acetate, and 0.15 g of ammonium bromide were placed into the same reactor as used in Example 1, and the oxidation reaction was conducted by introducing air into the reactor to maintain the oxygen partial pressure at 2 kg/cm$^2$ (total reaction pressure 25 kg/cm$^2$G) at a temperature of 100° C. One and half hours after the start of the reaction, 0.5 g of 30% aqueous solution of ammonium bromide was added to the reaction system, and the reaction was conducted for a total of 3 hours. The acetic acid and water were distilled off from the crude reaction product under reduced pressure. The resulting product was analyzed. Yields of dibasic acids were 72% for azelaic acid, 12% for dibasic acids containing up to 8 carbon atoms and 14% for dibasic acids having not less than 10 carbon atoms (total 98%), and yields of monocarboxylic acids were 71% for pelargonic acid, 22% for monocarboxylic acids having 5 to 8 carbon atoms and 5% for monocarboxylic acids having not less than 10 carbon atoms (total 98%), each relative to the unsaturated fatty acids contained in the starting commercial oleic acid.

EXAMPLE 3

To commercial oleic acid (100 g) was added 100 g of 88% aqueous solution of formic acid, and 24 g of 60% aqueous solution of hydrogen peroxide was added dropwise over a period of 1 hour while stirring the mixture at a temperature of 80° C. The mixture was reacted further for 3 hours, and the formic acid and water were distilled off under reduced pressure from the reaction mixture, giving 128 g of an oily substance, which was found by analysis to have an iodine value of 2.5, a vicinal hydroxyl value of 16 and a vicinal hydroxyl value after saponification of 231.

Into the same reactor as used in Example 1 were placed half of the oily substance obtained, 0.2 g of cobalt bromide, and 0.19 g of cerium acetate $(Ce(OAc)_3)$, and the reaction was conducted by introducing air into the reactor to maintain the oxygen partial pressure at 2 kg/cm$^2$ (total reaction pressure=30 kg/cm$^2$G) at a temperature of 110° C. Two hours after the start of the reaction, 0.4 g of tetrabromoethane was added to the reaction system and the reaction was continued for further 2 hours (total 4 hours). The resulting product was analysed. Yields of dibasic acids were 69% for azelaic acid, 15% for dibasic acids containing 5 to 8 carbon atoms and 12% for dibasic acids having not less than 10 carbon atoms (total 96%), and yields of monocarboxylic acids were 68% for pelargonic acid, 25% for monocarboxylic acids having 5 to 8 carbon atoms and 4% for monocarboxylic acids having not less than 10 carbon atoms (total 97%), each relative to the unsaturated fatty acids contained in the starting oleic acid.

EXAMPLE 4

To 100 g of commercial oleic acid were added 100 g of acetic acid and 0.3 g of concentrated sulfuric acid. While stirring the mixture, 24 g of 60% aqueous solution of hydrogen peroxide was added dropwise to the mixture at 80° C. over a period of 1 hour. The resulting mixture was further subjected to reaction at the same temperature for 2 hours and cooled. Sodium hydroxide was added to neutralize sulfuric acid and the acetic acid and water were distilled off. The residue was washed with water and dried, giving 131 g of an oily substance. Analysis of the oily substance showed that it had an iodine value of 1.3, a vicinal hydroxyl value of 49 and a vicinal hydroxyl value after saponification of 228.

In the same reactor as used in Example 1 were placed half of the oily substance, 0.7 g of cobalt naphthenate (containing 8% of cobalt), 0.8 g of manganese naphthenate (containing 6% of manganese) and 0.2 g of 40% aqueous solution of hydrobromic acid. While introducing air into the reactor, reaction was conducted at an oxygen partial pressure of 2 kg/cm$^2$ (reaction pressure of 30 kg/cm$^2$G) at a temperature of 110° C. for 4 hours. Analysis revealed that yeilds of dicarboxylic acids (total 96%) were 66% for azelaic acid, 18% for dicarboxylic acids containing 5 to 8 carbon atoms and 12% for dicarboxylic acids containing at least 10 carbon atoms, and that yields of monocarboxylic acids (total 95%) were 70% for pelargonic acid, 21% for monocarboxylic acids containing 5 to 8 carbon atoms and 4% for monocarboxylic acids containing at least 10 carbon atoms, each relative to the unsaturated carboxylic acids in the commercial oleic acid.

EXAMPLE 5

To 100 g of commercial oleic acid were added 100 g of tert-butyl alcohol, 1.3 g of tungstic acid $(H_2WO_4)$, 0.4 g of concentrated sulfuric acid, and 20 g of water, and the mixture was stirred at 50° to 60° C. A 20 g quantity of 60% aqueous solution of hydrogen peroxide was added dropwise to the mixture over a period of 1 hour while maintaining the mixture at 60° C. to continue reaction at the same temperature for 5 hours. After neutralization, the tert-butanol and water were vaporized under reduced pressure and the residue was washed with water. Analysis of the resulting oily substance (110 g) showed that it had an iodine value of 2, vicinal hydroxyl value of 242 and vicinal hydroxyl value after saponification of 273. Into the same reactor as used in Example 1 were placed half of the oily substance produced, 100 g of acetic acid and 0.5 g of cobalt bromide, and reaction was conducted at 100° C. and at an oxygen partial pressure of 1 kg/cm$^2$ (reaction pressure of 25 kg/cm$^2$G) while introducing air into the reactor. Thirty minutes after the temperature was elevated to 100° C., absorption of oxygen was initiated, followed by reaction for 7 hours. Analysis of the reaction product revealed that yields of dicarboxylic acids (total 92%) were 68% for azelaic acid, 15% for dicarboxylic acids containing 5 to 8 carbon atoms and 9% for dicarboxylic acids containing at least 10 carbon atoms and that yields of monocarboxylic acids (total 92%) were 66% for pelargonic acid, 22% for monocarboxylic acids containing 5 to 8 carbon atoms and 4% for monocarboxylic acids containing at least 10 carbon atoms, all relative to the unsaturated fatty acids in the commercial oleic acid.

EXAMPLE 6

A 6 g quantity of 88% aqueous solution of formic acid was added to 100 g of each of unsaturated fatty acids, methyl ester or soybean oil as shown below in Table 1. A specified amount of 60% aqueous solution of hydrogen peroxide was added dropwise to the mixture over a period of 1 hour while stirring the mixture at a temperature of 50° C. to 60° C., and then further reaction followed for 6 hours. The resulting reaction mixture was cooled and subjected to separation to give an oily substance. Into the same autoclave as used in Example 1 were placed half of the oily substance, 100 g of acetic acid, 0.19 g of cobalt acetate, 0.18 g of manganese acetate and 0.3 g of sodium bromide. The mixture ws heated to 100° C. with stirring at an oxygen partial pressure of 1.5 kg/cm$^2$ (reaction pressure 25 kg/cm$^2$G) while forcing air into the autoclave to continue reaction for 1.5 hours. Thereafter 0.3 ml quantity of 40% aqueous solution of hydrobromic acid and the resulting mixture was subjected to reaction for a total of 3 hours. Analysis of the reaction product thus obtained was conducted with the results shown in Table 1. In the case of methyl oleate and soybean oil, the resulting reaction mixture was subjected to hydrolysis to hydrolyze the remaining ester, and thereafter the desired products were collected and analyzed.

contemplated in high yields. It is also seen that the process of the invention gives the desired products in high yields even when the starting material is tall oil fatty acid, soybean oil or rapeseed oil which contains a great amount of dienoic acids or poly-enoic acids.

EXAMPLE 7

Commercial oleic acid was reacted in the same manner as in Example 1 with hydrogen peroxide to give an oily substance. Using 100 g of the oily substance, 100 g of acetic acid and catalysts as shown below in Table 2, oxidation was conducted under the conditions as indicated below in Table 2 to achieve cleavage of the double bond. Table 2 below shows the results.

TABLE 2

| | Reaction conditions | | | Yield of dicarboxylic acids (%) | | |
|---|---|---|---|---|---|---|
| | | Oxygen | | | | |
| Catalyst | Temp. (°C.) | partial pressure (kg/cm$^2$) | Reaction time (h) | At least 9 carbon atoms | 5 to 8 carbon atoms | Total |
| Co(OAc)$_2$80 mM, MnBr$_2$80 mM | 90 | 2.5 | 2.5 | 77 | 22 | 99 |
| CoBr$_2$10 mM, Mn(OAc)$_2$5 mM | 140 | 0.6 | 2.7 | 69 | 30 | 99 |
| Co(OAc)$_2$10 mM, Mn(OAc)$_2$5 mM, Ce(OAc)$_3$2 mM, Ni(OAc)$_2$5 mM, NaBr10 mM, HBr10 mM | 100 | 1.5 | 3.0 | 84 | 14 | 98 |
| Co(OAc)$_2$5 mM, Mn(OAc)$_2$5 mM, NaBr100 mM, HBr50 mM | 100 | 5.0 | 3.5 | 68 | 21 | 89 |

EXAMPLE 8

To 100 g of commercial oleic acid were added 38 g of t-butyl hydroperoxide, 200 g of ethyl benzene and 1.0 g of molybdenum naphthenate (containing 5% of molybdic acid) and the mixture was subjected to reaction for 3 hours at 80° C. and distilled under reduced pressure to remove the ethyl benzene, giving 106 g of an oily substance. Analysis of the oily substance showed that it had an iodine value of 3.6 and contained 1.5% oxirane oxygen (epoxide yield 27.8%). Into the same reactor as in Example 1 were placed half of the resulting oil substance, 100 g of acetic acid, 0.19 g of cobalt acetate, 0.18 g of manganese acetate and 0.15 g of ammonium bromide, and reaction was conducted at an oxygen partial pressure of 2 kg/cm$^2$ (reaction pressure of 25 kg/cm$^2$G). The crude reaction product was distilled under reduced pressure to remove the acetic acid and water. Analysis of the residue showed that yields of dicarboxylic acids were 71% for azelaic acid, 11% for dibasic acids containing 8 or less carbon atoms and 13% for dibasic acids containing at least 10 carbon atoms

TABLE 1

| Starting materials | | Amount of 60% hydrogen peroxide (g) | Yield of dicarboxylic acids (%)* | | | Yield of monocarboxylic acids (%)* | | |
|---|---|---|---|---|---|---|---|---|
| Kind | Iodine value | | At least 9 carbon atoms | 5 to 8 carbon atoms | Total | At least 9 carbon atoms | 5 to 8 carbon atoms | Total |
| Tall oil fatty acid | 133 | 37 | 75 | 16 | 91 | 27 | 57 | 84 |
| Purified fatty acid of soybean | 124 | 34 | 79 | 16 | 95 | 10 | 72 | 82 |
| Crude fatty acid of soybean | 127 | 35 | 73 | 14 | 87 | 8 | 74 | 82 |
| Purified fatty acid of rapeseed | 117 | 33 | 80 | 15 | 95 | 49 | 43 | 92 |
| Methyl oleate | 86 | 24 | 81 | 12 | 93 | 68 | 22 | 90 |
| Soybean oil | 133 | 37 | 75 | 16 | 91 | 11 | 71 | 82 |

*Yield relative to the unsaturated fatty acids which constitute the starting material Table 1 reveals that the process of the present invention gives the dicarboxylic and monocarboxylic acids as (total 95%) and that yields of monocarboxylic acids were 70% for pelargonic acid, 20% for monocarboxylic acids containing 5 to 8 carbon atoms and 5% for monocarboxylic acids containing at least 10 carbon atoms (total 95%), each relative to the unsaturated fatty acids in the commercial oleic acid.

EXAMPLE 9

Continuous reaction was conducted with use of the same titanium autoclave as used in Example 1 which was equipped with an inlet for liquids and an outlet for the reaction product. Used as the material was an oily substance produced by reacting hydrogen peroxide with commercial oleic acid in the same manner as in Example 2.

In the autoclave were placed 100 g of the oily substance, 100 g of acetic acid, 0.6 g of cobalt bromide, and 0.5 g of manganese acetate. The mixture was subjected to reaction at 100° C. and at an oxygen partial pressure of 1.5 kg/cm$^2$ (reaction pressure 25 kg/cm$^2$G) for 3 hours. Thereafter the reaction was continued for feeding a solution of acetic acid containing 300 g of the oily substance, 1.8 g of cobalt bromide and 1.5 g of manganese acetate per liter of the solution in an amount of 50 ml per hour with use of a metering pump while withdrawing the reaction product in an amount corresponding to the amount of the solution being fed. The oxygen partial pressure was maintained at about 1.5 kg/cm$^2$ by adjusting the feed rate of air.

After completing the reaction continued for 6 hours, the reaction product was analyzed with the results that yields of dicarboxylic acids were 65% for azelaic acid, 13% for dicarboxylic acids containing 5 to 8 carbon atoms and 12% for dicarboxylic acids containing at least 10 carbon atoms, and that yields of monocarboxylic acids were 64% for pelargonic acid, 12% for monocarboxylic acids containing 5 to 8 carbon atoms and 5% for monocarboxylic acids containing at least 10 carbon atoms, each relative to the unsaturated fatty acids in the commercial oleic acid.

COMPARISON EXAMPLE 1

Into the same autoclave as in Example 2 were placed half of the oily substance produced by reacting 100 g of commercial oleic acid and hydrogen peroxide in the same manner as in Example 2, 100 g of acetic acid, 0.19 g of cobalt acetate. The mixture was subjected to reaction at 100° C. and at an oxygen partial pressure of 2 kg/cm$^2$ (reaction pressure 25 kg/cm$^2$G) for 3 hours. The crude reaction product was analyzed in the same manner as in Example 2 and it was found that yields of dibasic acids were 22% for azelaic acid, 8% for dibasic acids containing 8 or less carbon atoms and 4% for dibasic acids containing at least 10 carbon atoms (total 34%) and that yields of monocarboxylic acids were 20% for pelargonic acid, 10% for monocarboxylic acids containing 5 to 8 carbon atoms and 2% for monocarboxylic acids containing at least 10 carbon atoms (total 32%), each relative to the unsaturated fatty acids contained in the commercial oleic acid.

EXAMPLE 10

To 100 g of commercial oleic acid (iodine value=91) were added 67 of acetic acid, 34 g of water and 0.3 g of concentrated sulfuric acid and the mixture was stirred. While maintaining the mixture at 80° C., a 23 g quantity of 60% aqueous solution of hydrogen peroxide was added dropwise to the mixture over a period of 1 hour. The mixture was further stirred with heating at 80% for 3 hours and then sodium hydroxide was added to neutralize the sulfuric acid. Then the acetic acid and water were distilled off under reduced pressure. The residue was washed with water and dried, giving 114 g of an oily substance. Analysis of the oily substance showed that it had an iodine value of 1.5, vicinal hydroxyl value of 169 and a vicinal hydroxyl value after saponification of 236.

Into a 500 ml titanium autoclave were placed half of the oily substance (57 g), 50 g of acetic acid, 0.16 g of cobalt bromide (CoBr$_2$.6H$_2$O), 0.12 g of cobalt chloride (CoCl$_2$.6H$_2$O) and 0.25 g of manganese acetate (Mn(OAc)$_2$.4H$_2$O). Air was introduced into the autoclave to maintain the oxygen partial pressure at 1.5 kg/cm$^2$ (reaction pressure 25 kg/cm$^2$G) and the mixture was stirred with heating. Absorption of oxygen started at about 80° C. and the temperature was maintained at 100° C. Each time of 1 and 2 hours after the initiation of the reaction, 0.2 ml of 20% aqueous solution of ammonium chloride was added by a paste pump. After the reaction continued for 3 hours, absorption of oxygen was scarcely observed, and the reaction mixture was cooled. The reaction mixture was distilled under reduced pressure to remove the acetic acid. A portion of the residue was methyl-esterified and analyzed by gas chromatography. The analysis revealed that yields of dicarboxylic acids were 70% for azelaic acid, 14% for dibasic acids containing 8 or less carbon atoms and 15% for dibasic acids containing at least 10 carbon atoms (total yield 99%), and that yields of monocarboxylic acids were 71% for pelargonic acid, 22% for monocarboxylic acids containing 5 to 8 carbon atoms and 5% for monocarboxylic acids containing at least 10 carbon atoms (total yield 98%), each relative to the unsaturated fatty acids contained in the commercial oleic acid. The reaction mixture was extracted with petroleum ether and the remaining crystals were suction filtered and recrystallized from water, giving white crystals having an azelaic acid purity of 82% and melting at 97° to 101° C. Yield 80% relative to the unsaturated fatty acids contained in the oleic acid.

EXAMPLE 11

A 6 g quantity of 88% aqueous solution of formic acid was added to 100 g of commercial oleic acid. While stirring the mixture at 50° to 60° C., 25 g of 60% aqueous solution of hydrogen peroxide was added dropwise to the mixture over a period of about 1 hour. After the mixture was further subjected to reaction at the same temperature for 8 hours, the reaction mixture was cooled and separated, giving 112 g of an oily substance. Analysis of the oily substance showed that it had an iodine value of 1.5, and 1.7% of oxirane oxygen (epoxide yield 29.8%). Into the same reactor as in Example 10 were placed half of the oily substance, 100 g of acetic acid, 0.19 g of cobalt acetate (Co(OAc)$_2$.4H$_2$O), 0.18 g of manganese acetate, 0.01 g of ammonium bromide and 0.07 g of ammonium chloride and oxidation was conducted by introducing air into the reactor at 100° C. and an oxygen partial pressure of 2 kg/cm$^2$ (reaction pressure 25 kg/cm$^2$G). One hour and half later, 0.27 g of 30% aqueous solution of ammonium chloride was added and reaction was effected for a total of 3 hours. The acetic acid and water were distilled off from the reaction crude mixture under reduced pressure. Analysis of the reaction product showed that yields of dibasic acids were 72% for azelaic acid, 14% for dibasic acids containing 8 or less carbon atoms and 12% for dibasic acids containing at least 10 carbon atoms (total 98%), and that yields of monocarboxylic acids were 71% for pelargonic acid, 22% for monocarboxylic acids containing 5 to 8 carbon atoms and 5% for monocarboxylic acids containing at least 10 carbon atoms (total 98%), each relative to the unsaturated fatty acids in the commercial oleic acid.

EXAMPLE 12

A 100 g quantity of 88% aqueous solution of formic acid was added to 100 g of commercial oleic acid, and the mixture was stirred. While maintaining the temperature at 80° C., 24 g of 60% aqueous solution of hydrogen peroxide was added dropwise over a period of 1 hour. The reaction was further continued for 3 hours and then the formic acid and water were distilled off under reduced pressure, giving 128 g of an oily substance having an iodine value of 2.5, vicinal hydroxyl value of 18 and vicinal hydroxyl value after saponification of 238. Into the same reactor as in Example 10 were placed half of the oily substance, 0.15 g of cobalt chloride ($CoCl_2.6H_2O$), 0.19 g of cerium acetate ($Ce(OAc)_3$) and 0.01 g of 47% aqueous solution of hydrobromic acid. The reaction was conducted by introducing air into the reactor at a temperature of 110° C. and at an oxygen partial pressure of 2 $kg/cm^2$ (reaction pressure 30 $kg/cm^2G$). Two hours later, 0.2 g of tetrachloroethane was added, and the mixture was subjected to reaction for 2 hours (total 4 hours). Analysis of the resulting reaction product showed that yields of dibasic acids were 76% for azelaic acid, 12% for dibasic acids containing at least 10 carbon atoms and 16% for dibasic acids containing 5 to 8 carbon atoms (total 95%) and that yields of monobasic acids were 65% for pelargonic acid, 24% for monobasic acids containing 5 to 8 carbon atoms and 6% for monobasic acids containing at least 10 carbon atoms (total 95%), each relative to the unsaturated fatty acids in the oleic acid.

EXAMPLE 13

In the same reactor as in Example 12 were placed 64 g of an oily substance produced by treating commercial oleic acid in the same manner as in Example 12, 0.7 g of cobalt naphthenate (containing 8% of cobalt), 0.8 g of manganese naphthenate (containing 6% of manganese) and 0.1 g of concentrated hydrochloric acid (35%). The reaction was conducted for 4 hours by introducing air into the reactor at a temperature of 110° C. and at an oxygen partial pressure of 2 $kg/cm^2$ (reaction pressure 30 $kg/cm^2G$). Analysis of the reaction product showed that yields of dibasic acids were 60% for azelaic acid, 16% for dibasic acids containing 5 to 8 carbon atoms and 10% for dibasic acids containing at least 10 carbon atoms (total yield of dibasic acids=86%), and that yields of monobasic acids were 63% for pelargonic acid, 18% for monobasic acids containing 5 to 8 carbon atoms and 4% for monobasic acids containing at least 10 carbon atoms (total yield of monobasic acids=85%), each relative to the unsaturated fatty acids in the oleic acid.

EXAMPLE 14

Continuous reaction was performed by use of the same titanium autoclave as used in Example 10 equipped with an inlet and an outlet for liquids. Into the autoclave were placed 100 g of an oily substance obtained by reacting commercial oleic acid with peroxide in the same manner as in Example 11, 0.4 g of cobalt chloride, 0.1 g of cobalt bromide, and reaction was conducted at a temperature of 110° C. and at an oxygen partial pressure of 1.5 $kg/cm^2$ (reaction pressure 25 $kg/cm^2G$) for 3 hours. Thereafter a solution of acetic acid containing 300 g of the oily substance, 1.2 g of cobalt chloride, 0.1 g of cobalt bromide and 1.5 g of manganese acetate per liter of the solution was fed to the reactor by a metering pump in an amount of 50 ml per hour and reaction was effected while drawing off the reaction product in an amount corresponding to that of the solution being fed. The oxygen partial pressure was maintained at about 1.5 $kg/cm^2$ by adjusting the feed rate of air. Analysis of the reaction product produced by 6 hours of reaction indicated that yields of dibasic acids were 64% for azelaic acid, 14% for dibasic acids containing 5 to 8 carbon atoms and 11% for dibasic acids containing at least 10 carbon atoms and that yields of monobasic acids were 64% for pelargonic acid, 10% for monobasic acids containing 5 to 8 carbon atoms and 4% for monobasic acids containing at least 10 carbon atoms, each relative to the unsaturated fatty acids in the commercal oleic acid.

EXAMPLE 15

To 160 g of 1-decene were added 100 g of acetic acid and 0.4 g of concentrated sulfuric acid and then 68 g of 60% aqueous solution of hydrogen peroxide was added dropwise to the mixture at 65° to 70° C. over a period of 1 hour, followed by further reaction at the same temperature for 5 hours. A 0.2 g quantity of sodium hydroxide was added to the reaction mixture and the acetic acid and water and the like were distilled off under reduced pressure. The residue was washed with water. The resulting oily substance (245 g) thus produced was found to have an iodine value of 2, a vicinal hydroxyl value of 140 and vicinal hydroxyl value after saponification of 293.

The oily substance was oxidized by air in the following manner. Into a 500 ml titanium autoclave were placed 100 g of the oily substance, 100 g of acetic acid, 0.66 g of cobalt bromide ($CoBr_2.6H_2O$) and 0.50 g of manganese acetate ($Mn(OCOCH_3)_2.4H_2O$). Air was introduced into the autoclave to maintain the reaction pressure at 25 $kg/cm^2G$ (oxygen partial pressure 2 $kg/cm^2$) and the reaction mixture was heated with stirring. Absorption of oxygen started at 80° C. At each time of 1 and 2 hours after initiation of the reaction at 100° C., 1 ml of 20% aqueous solution of ammonium bromide was added. After the reaction continued for a total of 3 hours, absorption of oxygen was scarcely observed. The reaction mixture was cooled and distilled under reduced pressure to remove the acetic acid. Further distillation under reduced pressure gave 71 g of a distillate. The distillate was analyzed by gas chromatography and was found to contain 6% by weight of short-chain fatty acids containing 4 to 7 carbon atoms, 6% by weight of caprylic acid, and 88% by weight of pelargonic acid. The yield of pelargonic acid was 85 mole % relative to the 1-decene.

EXAMPLE 16

A 39 g quantity of 88% aqueous solution of formic acid was added to 123 g of cyclohexene, and 102 g of 60% aqueous solution of hydrogen peroxide was added dropwise to the mixture at 65° to 70° C. over a period of 1 hour. Reaction was conducted at 80° C. for 6 hours. The formic acid, water and so on were distilled off under reduced pressure, giving 202 g of an oily substance. The oily substance was found to have an iodine value of 4, vicinal hydroxyl value of 407 and vicinal hydroxyl value after saponification of 658.

Into the same reactor as in Example 15 were placed 100 g of the oily substance, 100 g of acetic acid, 0.50 g of cobalt acetate (Co(OCOCH$_3$)$_2$.4H$_2$O), 0.63 g of cerium acetate (III) and 0.8 g of 47% aqueous solution of hydrobromic acid. Air was forced into the autoclave at 100° C. and reaction was conducted at a reaction pressure of 25 kg/cm$^2$G (oxygen partial pressure 2 kg/cm$^2$) for 2 hours. Thereafter 2 ml of 20% aqueous solution of ammonium bromide was added. The mixture was further reacted for 2 hours, and then absorption of oxygen was scarcely observed. The acetic acid and water were distilled off and the residue was further distilled under reduced pressure, giving 138 g of a solid distillate. The distillate was analyzed by gas chromatography and was found to contain 3% by weight of succinic acid, 10% by weight of glutaric acid, and 87% by weight of adipic acid. The yield of adipic acid was 82 mole % relative to the starting cyclohexene.

EXAMPLE 17

Into a titanium autoclave were added 100 g of the oily substance produced in the same manner as in Example 15 using 160 g of 1-decene, together with 100 g of acetic acid, 0.33 g of cobalt bromide (CoBr$_2$.6H$_2$O), 0.25 g of cobalt acetate (co(OCOCH$_3$)$_2$.4H$_2$O), 0.50 g of manganese acetate (Mn(OCOCH$_3$)$_2$.4H$_2$O), and 0.17 g of concentrated hydrochloric acid (35%). Air was forced into the autoclave at 100° C. and reaction was conducted at a reaction pressure of 25 kg/cm$^2$G (oxygen partial pressure 2 kg/cm$^2$). Each time of 1 and 2 hours after initiation of the reaction, 1 ml of 10% aqueous solution of ammonium chloride was added. The reaction was continued for a total of 3 hours. Thereupon absorption of oxygen was scarcely observed. After removal of the acetic acid by distillation, further distillation under reduced pressure followed, giving 70 g of a distillate. The distillate was analyzed by gas chromatography and was found to contain 6% by weight of short-chain fatty acids containing 4 to 7 carbon atoms, 7% by weight of caprylic acid and 87% by weight of pelargonic acid. The yield of pelargonic acid was 85 mole % relative to the starting 1-decene.

EXAMPLE 18

Into the same autoclave as in Example 15 were placed 100 g of the oily substance produced in the same manner as in Example 15 using 160 g of 1-decene, together with 100 g of acetic acid, 0.48 g of cobalt chloride (CoCl$_2$.6H$_2$O), 0.50 g of manganese acetate (Mn(OCOCH$_3$)$_2$.4H$_2$O) and 0.17 g of concentrated hydrochloric acid (35%). Air was forced into the autoclave at 100° C. and reaction was conducted at a reaction pressure of 25 kg/cm$^2$G (oxygen partial pressure 2 kg/cm$^2$). Each time of 1 and 2 hours after initiation of the reaction, 1 ml of 10% aqueous solution of ammonium chloride was added. The reaction was continued for a total of 4 hours. After removal of the acetic acid by distillation, further distillation under reduced pressure followed, giving 57 g of a distillate. The distillate was analyzed by gas chromatography and was found to contain 6% by weight of short-chain fatty acids containing 4 to 7 carbon atoms, 7% by weight of caprylic acid and 84% by weight of pelargonic acid. The yield of pelargonic acid was 65 mole % relative to the starting 1-decene.

COMPARISON EXAMPLE 2

Into the same autoclave as in Example 15 were placed 100 g of the oily substance produced in the same manner as in Example 15 using 160 g of 1-decene, together with 100 g of acetic acid, 0.50 g of cobalt acetate (Co(OCOCH$_3$)$_2$.4H$_2$O) and 0.50 g of manganese acetate (Mn(OCOCH$_3$)$_2$.4H$_2$O). Air was forced into the autoclave at 100° C. and reaction was performed at a reaction pressure of 25 kg/cm$^2$G (oxygen partial pressure of 2 kg/cm$^2$) for 3 hours. After completion of the reaction, the acetic acid was removed by distillation and further distillation under reduced pressure gave 19 g of a distillate. The distillate was analyzed by gas chromatography and was found to contain 7% by weight of short-chain fatty acids containing 4 to 7 carbon atoms, 19% by weight of caprylic acid and 74% by weight of pelargonic acid. The yield of pelargonic acid was 20 mole % relative to the 1-decene.

As seen from the above, when using a catalyst free from a bromine and chlorine compound, aliphatic carboxylic acid is given in markedly low yields.

We claim:

1. A process for preparing carboxylic acid, the process comprising subjecting an oxidation product produced by reacting a peroxide with (a) unsaturated aliphatic monocarboxylic acid having at least one unsaturated bond in the carbon chain and containing 6 to 24 carbon atoms or its ester or (b) cyclic and/or acyclic aliphatic olefin having at least one unsaturated bond in the carbon chain to oxidation by oxygen or oxygen-containing gas in the presence of a catalyst comprising (i) at least one heavy metal, complex or compound thereof and (ii) at least one member selected from the group consisting of bromine or compound thereof and chlorine or compound thereof.

2. A process as defined in claim 1 wherein the unsaturated aliphatic monocarboxylic acid is oleic acid, linoleic acid, linolenic acid, eleostearic acid, parinaric acid, elaidic acid, ricinoleic acid, caproleic acid, myristoleic acid, palmitoleic acid, petroselinic acid, erucic acid, brassidic acid, arachidonic acid, a mixture thereof, a fatty acid mixture produced by hydrolyzing a vegetable oil or an animal oil, or tall oil fatty acid.

3. A process as defined in claim 1 wherein the ester is a C$_1$–C$_5$ alkyl ester or a glyceride of the unsaturated aliphatic monocarboxylic acid.

4. A process as defined in claim 1 wherein the cyclic and/or acyclic aliphatic olefin has 5 to 18 carbon atoms.

5. A process as defined in claim 4 wherein the cyclic aliphatic olefin has 5 to 18 carbon atoms.

6. A process as defined in claim 5 wherein the cyclic aliphatic olefin is cyclopentene, cyclohexene, cyclooctene or dicyclopentadiene.

7. A process as defined in claim 4 wherein the acyclic aliphatic olefin has 6 to 18 carbon atoms.

8. A process as defined in claim 7 wherein the acyclic aliphatic olefin is 1-hexene, 3-hexene, 1-heptene, 1-octene, 2-octene, 4-octene, 1-nonene, 1-decene, 5-decene, 6-decene, 1-dodecene, 1-tetradecene, 7-tetradecene, 1-hexadecene, 8-hexadecene, 1-octadecene or 9-octadecene.

9. A process as defined in claim 1 wherein the oxidation product has vicinal diol group; epoxy group; hydroxyl group and ether group; hydroxyl group and ester group; ester group and ether group; ester group and ester group; or ether group and ether group.

10. A process as defined in claim 1 wherein the peroxide is hydrogen peroxide, inorganic peroxide, organic peracid or organic hydroperoxide.

11. A process as defined in claim 1 wherein the peroxide is hydrogen peroxide, pertungstic acid, permolybdic acid, permanganic acid, performic acid, peracetic acid, perbenzoic acid, m-chloroperbenzoic acid, cumene hydroperoxide or t-butyl hydroperoxide.

12. A process as defined in claim 1 in which the heavy metal, complex or compound thereof is any of metals having atomic numbers of 23 to 32, 39 to 51 and 57 to 84, and their salts, complexes, oxides or hydroxides.

13. A process as defined in claim 1 in which the heavy metal, complex or compound thereof is cobalt metal, manganese metal, cerium metal or nickel metal; a carboxylic acid salt or inorganic acid salt of cobalt, manganese, cerium or nickel, the carboxylic acid being an aliphatic carboxylic acid having 1 to 20 carbon atoms, naphtenic acid, or benzoic acid or phthalic acid which are optionally substituted with halogen or methyl group on the phenyl ring, and the inorganic acid being hydrogen chloride, hydrogen bromide, hydrogen iodide, hydrogen fluoride, carbonic acid, sulfuric acid, phosphoric acid, chromic acid or nitric acid; a complex of cobalt, manganese, cerium or nickel having as a ligand acetylacetone, ammonia, pyridine or aniline; an oxide of cobalt, manganese, cerium or nickel; or a hydroxide of cobalt, manganese, cerium or nickel.

14. A process as defined in claim 1 wherein the bromine or compound thereof is molecular bromine; hydrogen bromide; bromide, hypobromite, bromate of ammonia, alkali metal, alkaline earth metal, cobalt, manganese, cerium or nickel; or lower hydrocarbon bromide.

15. A process as defined in claim 1 in which the bromine or compound thereof is at least one member selected from the group consisting of hydrogen bromide, ammonium bromide, sodium bromide, cobalt bromide, manganese bromide, cerium bromide, nickel bromide, tetrabromoethane and tribromoethane.

16. A process as defined in claim 1 in which the chlorine or compound thereof is molecular chlorine; hydrogen chloride; chloride, chlorate, hypochlorite or perchlorate of ammonia, alkali metal, alkaline earth metal, cobalt, manganese, cerium or nickel; or lower hydrocarbon chloride.

17. A process as defined in claim 1 in which the chlorine or compound thereof is at least one member selected from the group consisting of hydrogen chloride, ammonium chloride, sodium chloride, cobalt chloride, manganese chloride, cerium chloride, nickel chloride, tetrachloroethane and trichloroethane.

18. A process as defined in claim 1 wherein the catalyst comprises at least two heavy metals, complexes or compounds thereof each of which contain different kind of heavy metal.

19. A process as defined in claim 18 wherein the heavy metals, complexes or compounds thereof are cobalt metal, manganese metal, cerium metal or nickel metal; acetate, naphthenate, 2-ethyl-hexanoate, stearate, chloride, bromide or carbonate of cobalt, manganese, cerium or nickel; acetylacetonate complex of cobalt, manganese, cerium or nickel; an oxide of cobalt, manganese, cerium or nickel; or a hydroxide of cobalt, manganese, cerium or nickel.

20. A process as defined in claim 18 wherein the bromine or compound thereof is at least one member selected from the group consisting of hydrogen bromide, ammonium bromide, sodium bromide, cobalt bromide, manganese bromide, cerium bromide, nickel bromide, tetrabromoethane, tribromoethane, and the chlorine or compound thereof is at least one member selected from the group consisting of hydrogen chloride, ammonium chloride, sodium chloride, cobalt chloride, manganese chloride, cerium chloride, nickel chloride, tetrachloroethane and trichloroethane.

21. A process as defined in claim 1 in which the heavy metal, complex or compound thereof is used in an amount of 0.05 to 10 g per liter of the reaction mixture when calculated as metal.

22. A process as defined in claim 1 in which the bromine or compound thereof and/or the chlorine or compound thereof are/is used in an amount of 0.1 to 100 equivalents based on heavy metal atom when calculated as bromine atom and/or chlorine atom.

23. A process as defined in claim 1 in which the oxidation is conducted at a total reaction pressure of 0 to 100 kg/cm$^2$G and an oxygen partial pressure of 0.1 to 10 kg/cm$^2$.

24. A process as defined in claim 1 in which the oxidation is conducted at a temperature of 60° to 200° C.

* * * * *